United States Patent [19]

Meens et al.

[11] Patent Number: 5,858,727
[45] Date of Patent: Jan. 12, 1999

[54] SECRETION OF OUTER MEMBRANE PROTEINS OF GRAM-NEGATIVE BACTERIA BY MEANS OF GRAM-POSITIVE HOST ORGANISMS

[75] Inventors: Jochen Meens, Aachen; Michael Klose; Hermann Sahm, both of Jülich; Roland Freudl, Düren, all of Germany

[73] Assignee: Forschungszentrum Julich GMBH, Julich, Germany

[21] Appl. No.: 676,378

[22] PCT Filed: Nov. 21, 1994

[86] PCT No.: PCT/DE94/01394

§ 371 Date: Jul. 18, 1996

§ 102(e) Date: Jul. 18, 1996

[87] PCT Pub. No.: WO95/20048

PCT Pub. Date: Jul. 27, 1995

[30] Foreign Application Priority Data

Jan. 19, 1994 [DE] Germany .......................... 44 01 419.8

[51] Int. Cl.[6] ...................... C07K 14/195; C07K 14/245; C12N 15/31; C12N 15/62
[52] U.S. Cl. .................. 435/69.7; 435/320.1; 435/252.3; 435/69.8; 530/350; 530/825; 536/23.4; 424/192.1
[58] Field of Search .................................. 435/69.1, 69.8, 435/172.3, 252.31, 320.1, 69.7, 252.3, 23.4; 530/350, 825; 536/23.1, 23.7, 24.1, 23.4; 424/192.1

[56] References Cited

PUBLICATIONS

Meens, J. et al. *Applied & Environmental Microbiology* 63(7): 2814–2820 (1997).

Meens et al. *Molecular Microbiology* 9(4): 847–855 (1993).

Puohiniemi, R. et al. *FEMS* 106: 105–110 (1993).

*Primary Examiner*—Dian C. Jacobson
*Attorney, Agent, or Firm*—Herbert Dubno; Jonathan Myers

[57] ABSTRACT

The invention relates to a process for producing outer membrane proteins of gram-negative bacteria by gram-positive host cells. To this end, a gene structure containing a gene coded for an outer membrane protein is constructed; in front of this gene there is a pro-gene sequence which codes for a propeptide of an export protein of a gram-positive bacterium. In front of the pro-gene sequence there is a pre-gene sequence which codes for a signal peptide of an export protein of a gram-positive bacterium. After the cloning of a gene structure thus constructed into a vector and transformation into a gram-positive bacterium, the outer membrane protein is expressed with a signal peptide and propeptide, transported through the membrane of the gram-positive host cell and released into the test of the culture.

9 Claims, 3 Drawing Sheets

NUCLEOTIDE SEQUENCE OF THE OLIGOTIDE SYSTEMS USED:

K8: TATCTTCGGAGCGGCTCTGCGCTACGGTAG
E.coli ompA; BASE PAIRS 1083-1111

K23: AGGTGCTGCTTTTACGTATGGTTTTTGCGCT
S.carnosus Lipase; BASE PAIRS 946-978

FIG.1

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

TATCTTTCGG AGCGCTCTGC GCTACGGTAG        30

( 2 ) INFORMATION FOR SEQ ID NO:2:

( i ) SEQUENCE CHARACTERISTICS:
 ( A ) LENGTH: 33 base pairs
 ( B ) TYPE: nucleic acid
 ( C ) STRANDEDNESS: single
 ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

AGGTGCTGCT TTTACGTATG GTTTTTTTGC GCT    33

( 2 ) INFORMATION FOR SEQ ID NO:3:

( i ) SEQUENCE CHARACTERISTICS:
  ( A ) LENGTH: 18 base pairs
  ( B ) TYPE: nucleic acid
  ( C ) STRANDEDNESS: double
  ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
  ( A ) NAME/KEY: CDS
  ( B ) LOCATION: 1..18

( x i ) SEQUENCE DESCRIPTION: SEQ ID NO:3:

AAA  CCA  ACA  GTA  AAA  GCA    18
Lys  Pro  Thr  Val  Lys  Ala
 1              5

( 2 ) INFORMATION FOR SEQ ID NO:4:

( i ) SEQUENCE CHARACTERISTICS:
  ( A ) LENGTH: 6 amino acids
  ( B ) TYPE: amino acid
  ( D ) TOPOLOGY: linear ( i i ) MOLECULE TYPE: protein ( x i ) SEQUENCE DESCRIPTION: SEQ ID NO:4:

Lys  Pro  Thr  Val  Lys  Ala
 1              5

( 2 ) INFORMATION FOR SEQ ID NO:5:

( i ) SEQUENCE CHARACTERISTICS:
  ( A ) LENGTH: 18 base pairs
  ( B ) TYPE: nucleic acid
  ( C ) STRANDEDNESS: double
  ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
  ( A ) NAME/KEY: CDS
  ( B ) LOCATION: 1..18

( x i ) SEQUENCE DESCRIPTION: SEQ ID NO:5:

GCG  CAG  AGC  GCT  CCG  AAA    18
Ala  Gln  Ser  Ala  Pro  Lys
                 10

(2) INFORMATION FOR SEQ ID NO:6:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO:6:

```
Ala  Gln  Ser  Ala  Pro  Lys
 1                     5
```

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 1..18

(xi) SEQUENCE DESCRIPTION: SEQ ID NO:7:

```
AAA  CCA  TAC  GCT  CCG  AAA                          18
Lys  Pro  Tyr  Ala  Pro  Lys
                10
```

(2) INFORMATION FOR SEQ ID NO:8:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO:8:

```
Lys  Pro  Tyr  Ala  Pro  Lys
 1                     5
```

SECRETION OF OUTER MEMBRANE PROTEINS OF GRAM-NEGATIVE BACTERIA BY MEANS OF GRAM-POSITIVE HOST ORGANISMS

FIELD OF THE INVENTION

The invention relates to a process for producing outer membrane proteins recoverable from the culture supernatant of Gram-negative bacteria from Gram-positive host cells, a gene structure capable of expressing the outer membrane proteins, a vector containing a gene structure capable of expressing the outer membrane protein, Gram-positive host cells containing said gene structure, outer membrane proteins expressed by the gene structure and a method of using the outer membrane proteins.

BACKGROUND OF THE INVENTION

Proteins from the outer membrane of Gram-negative bacteria are primarily exposed on the cell surface of these bacteria and in the case of pathogenic bacteria serve as possible attack points for the recognition of the bacteria by the immune system of the infected host.

It is thus desirable, with the aid of purified outer membrane proteins by inoculation to achieve protection of the host against the corresponding bacterium (Smyth, C. J. (1985) Immunology of outer membrane proteins of Gram-negative bacteria. In: Immunology of the Bacterial Cell Envelope (Stewart-Tull, D. E. S., Davies, M.; eds.) John Wiley and Sons Ltd. Pp. 177–201). A further possible use of isolated membrane proteins is their use as antigen in diagnostic test systems.

One way for recovery of the proteins is their isolation from the outer membrane Gram-negative bacteria. It is, however, problematic in that case that the outer membrane proteins have a high affinity to the lipopolysaccharide localized in the outer membrane so that the proteins can only be separated with difficulty from these endotoxins (Nikaido, H., Vaara M. (1985) Molecular basis of bacterial outer membrane permeability. Microbio). Rev. 49, 1–32). It is desirable to provide a way of producing outer membrane proteins which utilizes Gram-positive bacteria for their synthesis and which have an outer membrane with no lipopolysaccharide. One can expect that with these organisms endotoxin free outer membrane proteins can be recovered.

There are already different outer membrane proteins of Gram-negative bacteria (e.g. OmpA, OmpF) which are expressed intracellularly in the Gram-positive bacterium *Bacillus subtilis* (Puohiniemi, R., Butcher, S., Tarkka, E., Sarvas, M., (1991) High level production of *Escherichia coli* outer membrane proteins OmpA and OmpF intracellularly in *Bacillus subtilis*. FEMS Micro-biol. Lett. 83, 29–34). It has also been sought to export outer membrane proteins through the cytoplasmic membrane of Gram-positive bacteria for which secretory proteins are used for channeling in the exportation step and are necessary for the subsequent membrane transport and are fused to the outer membrane proteins: for example, a fusion of the membrane protein with the 298 aminoacid secretory protein α-amylase *Bacillus amyloliquefacines* is effected. In all of these cases, the expected secretion or transport of such fused membrane proteins is not found to occur (Kallio, P., Simonen, M., Pavla, I., Sarvas, M. (1986), Synthesis of OmpA protein of *Escherichia coli* K12 in *Bacillus subtilis*, J. Gen. Microbiol. 132, 677–678; Puohiniemi, R., Simonen, M., Muttilainen, S., Himanen, J.-P., Sarvas, M. (1992), Secretion of the *Escherichia coli* outer membrane proteins OmpA and OmpF in *Bacillus subtilis* is blocked at an early intracellular step., Mol. Microbiol. 6, 981–990; Simonen, M., Tarkka, E., Puohiniemi, R., Sarvas, M. (1992), Incompatibility of outer membrane proteins OmpA and OmpF of *Escherichia coli* with secretion in *Bacillus subtilis*: Fusions with secretable peptides, FEMS (Microbiol. Lett. 100, 233–242). By contrast, one finds instead, after expression, an outer membrane protein of *Escherichia coli* together with the authentic Gram-negative signal peptide in *Bacillus subtilis*, a transport through its cytoplasmic membrane but with the protein remaining cell associated, i.e. not secreted into the culture medium (Meens, J., Frings, E., Klose, M., Freudi, R. (1993), An outer membrane protein (OmpA) of *Escherichia coli* can be translocated across the cytoplasmic membrane of *bacillus subtilis*, Mol. Microbiol. 9, 847–855).

OBJECT OF THE INVENTION

The object of the invention initially is to provide a process which enables outer membrane proteins of Gram-negative bacteria to be so produced by Gram-positive bacteria that the outer membrane proteins are both transported through the membrane and are recoverable from the culture supernatant.

SUMMARY OF THE INVENTION

To achieve this object, initially a gene construct is fabricated that contains a gene coding for an outer membrane protein and, ahead of this gene, a progene sequence coding for a propeptide of an export protein of a Gram-positive bacterium, and, ahead of this gene sequence, a pregene sequence coding for a signal peptide of an export protein of a Gram-positive bacterium. Thus, the pre-pro-gene sequences can stem from only a single Gram-positive bacterium or also from two different Gram-positive bacteria. The individual gene segments can be isolated, for example, by the polymerase chain reaction (PCR) and coupled by ligation with one another. Finally, the so constructed gene structure is cloned in a vector with the gene positive bacterium which can be replicated or can be introduced into the chromosome by signal crossing to incorporate the gene structure in the chromosome of the Gram-positive host bacterium. Thus, for example, for the use of *Staphylococcus carnosus* as a vector, pC 194 or for the use of *Bacillus subtilis* as a vector pUB110 is suitable. The promoter required ahead of the gene construct can be constructed either together with the gene structure or already provided on the vector used. The vector is, finally, transformed in a Gram-positive bacterium in accordance with commercial methods, whereafter the outer membrane protein is not only expressed with signal peptide and propeptide, but is additionally transported through the membrane of the Gram-positive host cell and liberated in the culture medium.

In principal, any optional Gram-positive bacteria is suitable as the host cell to the extent only that vectors and transformation systems exist for them. Preferred, however, are especially those Gram-positive host cells which show little protease activities in the culture medium. In these cases, the liberated proteins remain stable in the medium over long time periods.

BRIEF DESCRIPTION OF THE DRAWING

FIG. 1 gives the structures of the oligonucleotide mutagenic agents K8 and K23 respectively.

SPECIFIC DESCRIPTION OF THE DRAWINGS

Figure 2:
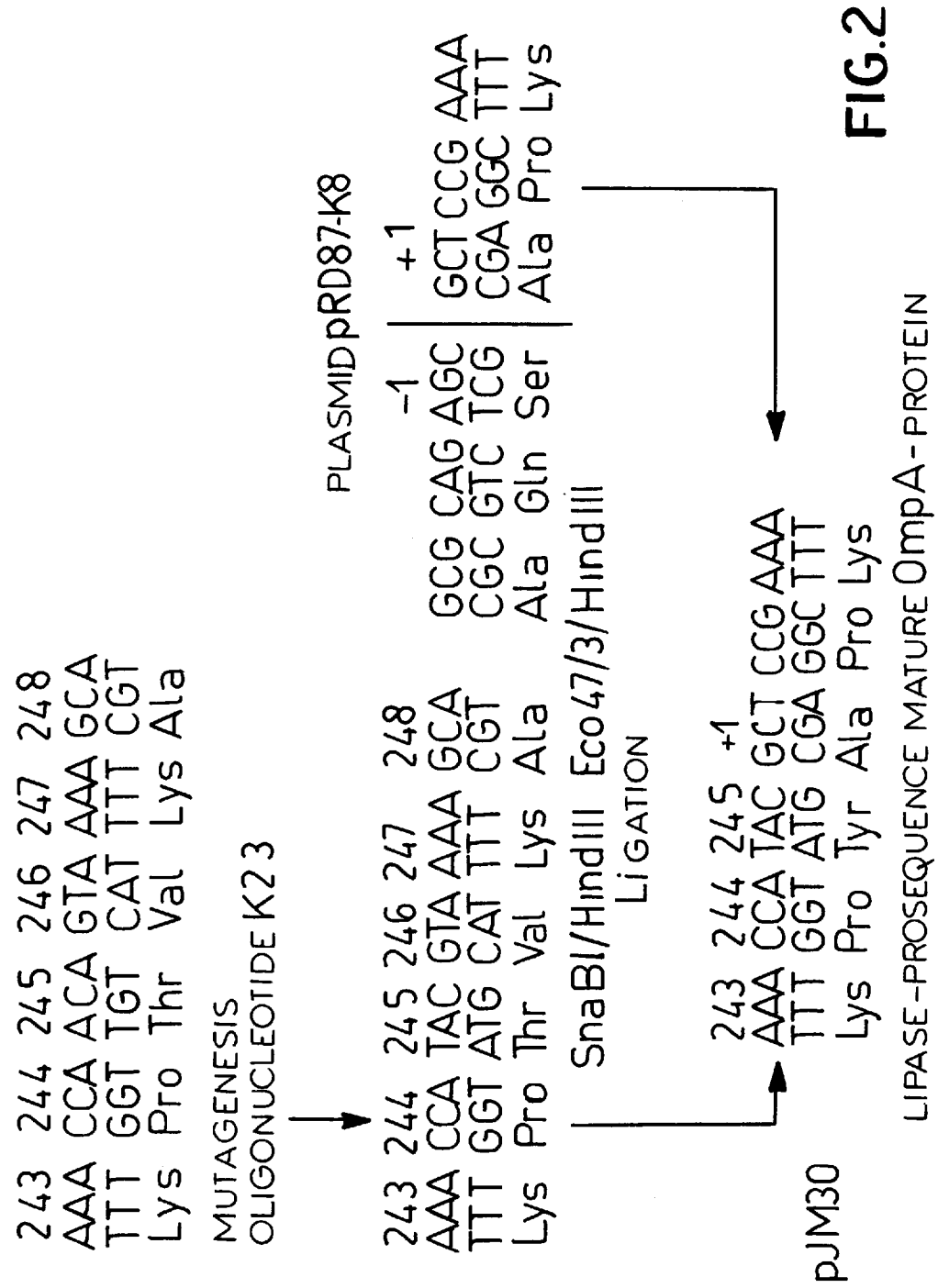
FIG. 2 is a diagram showing the steps involved in the construction of pJM30 which includes a gene construct containing an outer membrane protein coding gene from a gram negative bacterium ahead of which is located a progene sequence from a gram positive bacterium, the gene construct capable of expressing a fusion protein containing both the corresponding outer membrane protein and propeptide.

In FIG. 2 nucleotide and amino acid sequences at the fusion point of lipase prosequence and mature OmpA are disclosed.

The triplets or amino acids directly ahead of or behind the signal peptidase cleavage are indicated with −1/+1.

The triplets or amino acids at the transition from prosequence and mature lipase are numbered as 243 through 248.

Uppermost row: The wild type sequence of the lipase gene (right column/Plasmid pJM1)

Middle row: The sequence after oligo nucleotide-control mutagenesis in the Plasmid pJM1-K23 or PRO87-K8 changed bases and amino acids is shown.

Lowermost row: The sequence at the fusion point in the Plasmid pJM30 is shown.

Figure 3:
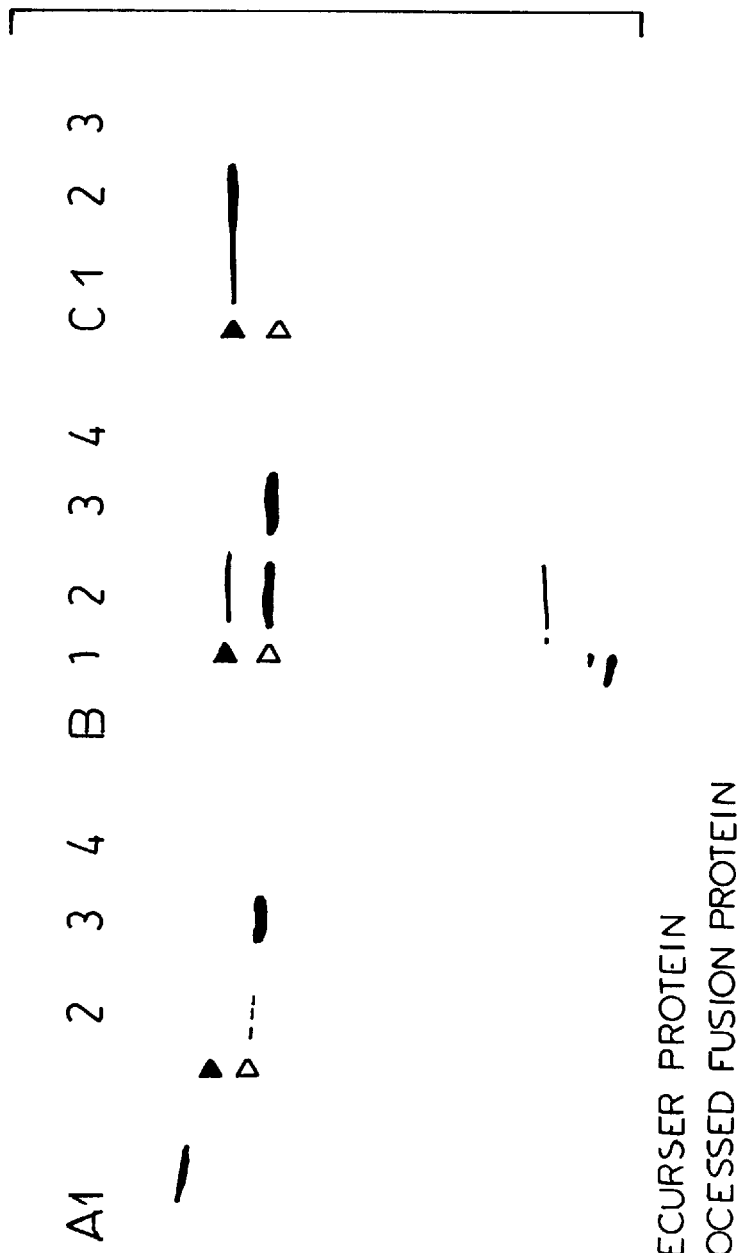
FIGS. 3a and 3b show a Western blot analysis using propeptide specific antibodies and outer membrane protein specific antibodies of the fusion protein prepared according to FIG. 2.
FIG. 3c shows a Western blot analysis of the proteins liberated by protoplastic cells of the strain TM300/pJM30 treated with trypsin.

In FIG. 3 evidence of the lipase in the OmpA fusion protein is shown in the S. carnosus strain TM300/pJM30 according to Western Blot analysis with lipase specific antibodies (A) or OmpA specific antibodies (BNC).

Cell proteins (Trace 2) and culture supernatant (Trace 3) are separately applied.

Trace 4: Total protein probe of TM300.

Trace 1(a): Prolipase from the culture supernatant of TM300/pLipPS1.

Trace 1(b) OmpA protein in E. Coli strain UH203/PRO87 after induction. The dark triangles stand for precursor protein and the light triangles stand for processed fusion protein.

C. Trying directed protoplastic cells of the strain TM300/pJM30.

Trace 1: protoplast without trypsin treatment
Trace 2: Trypsin treated intact protoplast
Trace 3: Trypsin treated after ultrasonic breakup.

EXAMPLE

Initially a plasmid (pJM30) is constructed that contains the gene of the mature outer membrane protein OmpA of *Escherichia coli*, fused with the gene coding for the pre-prosequence of a lipase from *Staphylococcus hyicus*. After transformation of the Plasmid in *Staphylococcus carnosus*, the secretion of the $pRO_{(Lip)}$-OmpA-fusion protein is detected:

a) Construction of the Plasmid pJM30.

The lipase gene from *Staphylococcus hyicus* is available in the Plasmid pLipPS1 (W. Liebl et al. (1986): Studies on lipase directed export of *Escherichia coli* β-lactamase in *Staphylococcus carnosus*. Mol. Gen. Genet. 204: 166–173). The expression of the lipase gene is effected constitutively and is controlled by the endogenous lipase promoter. In order to be able to isolate a promoterless lipase gene, a PstI-linker is ligated in the plasmid pLipPS1 at an AccI cleavage location which is located 60 Bp above the translation starting between the postulated promoter region (F. Götz et al. (1985): Complete nucleotide sequence of the lipase gene from *Staphylococcus hyicus* cloned in *Staphylococcus carnosus*. Nucl. Acids Res. 13: 3895–3906) and the lipase structure gene. The so constructed plasmid pLipPS1-Pl is transformed in *Staphylococcus carnosus* TM300 (F. Götz et al. (1987): Improvements of protoplast transformation in *Staphylococcus carnosus*. FEMS Microbiol. Letters 40: 285–288).

From the plasmid pLipPS1-Pl, the promoterless lipase gene is isolated as a 2.04 kB PstI fragment. This fragment is then ligated in the PstI cleavage site of the Plasmid pUC18 (C. Yanisch-Perron et al. (1985): Improved M13 phage cloning vectors and host strains: Nucleotide sequences of M13mp18 and pUC19 vectors. Gene 33: 103–119) which previously was filled by the SalI cleavage site. The ligation product is transformed in the *E.coli* strain JM109 and the resulting transform is tested for expression of the lipase gene. This leads to isolation of the Plasmid pJM1, in which the lipase gene has the desired orientation under the inducible control of the lac-promoter/operator system.

In the *S. hyicus* culture medium, the prolipase (comprised of the prosequence and mature lipase) is decomposed by a hitherto unknown extracellular protease to the mature lipase. The splitting between prosequence and mature lipase is effected between the amino acids $Thr^{245}$ and $Val^{246}$ (M. Van Oort et al. (1989): Purification and substrate specificity of *Staphylococcus hyicus*. Biochem. 28: 9278–9285).

For the construction of a gene which codes for a fusion of signal sequence and prosequence of the *S. hyicus* lipase with the mature part of the OmpA protein, a SnaBJ cleavage site is formed in the lipase gene at the position corresponding to the aminoacid $Thr^{245}/Val^{246}$ cleavage. As a template for the mutagenesis, a 1.3 kB SalI/HindIII fragment of the lipase gene (isolated from pJM1), which codes for a part of the prosequence and the entire mature lipase, is cloned in the vector M13mp18. The mutagenesis is carried out with the oligonucleotide K23 (FIG. 1) in accordance with the Kunkel method (Kunkel, T. (1985) Rapid and efficient site-specific mutagenesis without phenotypic selection, Proc. Natl. Acad. Sci. U.S.A., 82, 488–492).

From a clone with the desired base exchange, the fragment is isolated and returned to the plasmid pJM1 (plasmid pJM1-K23).

For construction of the OmpA gene, in which the region coding for the signal sequence has been deleted, by mutagenesis with the oligonucleotide K8 (FIG. 1) an Eco47/3 cleavage is inserted at the position which corresponds to the signal peptidase cleavage site. As a template, a 1.1 kB EcoR1/BamH fragment cloned in the vector M13mp18, with the OmpA gene from the plasmid P87 is used. From the clone with the desired base exchange, the fragment is isolated and reinserted in the plasmid pRD8-K8). From the plasmid pJM1-K23, the region coding for the mature lipase is removed by SnaB1/HindIII digestion and replaced by the Eco47/3/HindIII fragment of the plasmid PRD87-K8 which codes for the mature OmpA protein (FIG. 2).

The resulting plasmid pJM3 carries the desired hybrid gene under the control of the lac-promoter/operator region. For the expression in *S. carnosus*, the hybrid gene from the plasmid pJM3 is isolated on a 1.8 kB Pst1 fragment and ligated in the vector pLipPS1-P which has been removed from the lipase gene by PstI partial digestion. The general gene technology methods like the splitting of DNA with restriction endonuclease, ligation of DNA fragments and transformation of *E. coli* are carried out in accordance with Sambrook et al (1989) (J. Sambrook et al. (1989): Molecular cloning. A Laboratory Manual, 2nd edn. Cold Spring Harbor, N.Y.: Cold Spring Harbor Laboratory Press).

b) Secretion of the Pro$_{(Lip)}$-OmpA Fusion Protein in the *Staphylococcus carnosus* TM300 Strain The expression of the Pro$_{(Lip)}$-OmpA gene in the plasmid pJM30 is controlled by the lipase promoter and is effected therefore constitutively. Cells of the *S. carnosus* strain TM300/pJM30, deposited at the DSM on 1 Oct. 1994 under the number 8892 are cultured for 12 hours at 37° C. Cells and culture medium are processed separately. After gel electrophoresis separation of the proteins a Western Blot is carried out with both the lipase specific and the OmpA specific antibodies. The results are shown in FIG. 3*a/b*.

The Pro$_{(Lip)}$-OmpA gene codes for a 570 amino acid fusion protein with a calculated molecular weight of 72.2 kDa. After splitting the amino acid signal sequence off, the calculated molecular weight of the processed fusion protein amounts to 67.4 kDa. In the culture supernatant of the strain TM300/pJM30, a protein band is detected with an apparent molecular weight of about 78 kDa which shows a clear reaction with both antibodies (FIG. 3*a/b*, Trace 3). This apparently is the fusion protein which has been processed by translocation and liberated in the medium. In the cell protein fraction two protein bands with an apparent molecular weight of about 78 kDa and 82 kDa are found and which also reacts with both antibodies.

The exact localization of these proteins is effected by trypsin treatment of protoplastic cells of TM300/pJM30 (FIG. 3*c*). In the untreated protoplastic probe (FIG. 3*c*; Trace 1) the amount of the 78 kDa protein is clearly less than in the nonprotoplastic cells (FIG. 3*b*; Trace 2). The amount of 82 kDa protein is, by contrast, the same in both probes (equivalent cell proteins quantities applied). In the trypsin treatment, the 78 kDa is completely digested while the 83 kDa protein remains stable (FIG. 3*c*; Trace 2). After ultrasonic rupture of the protoplasts, both proteins are completely decomposed (FIG. 3*c*; Trace 3). The intactness of the protoplast can be determined by a Western Blot with antibodies against the chloramphenicol-acetyl transferase which is located in the cytoplasm, which is coded for by the Plasmid pJM30.

The difference between the calculated molecular weight and the molecular weight determined by SDS-Polyacrymide gel electrophesis is potentially attributable to the lipase component of the fusion protein. The prolipase shows for hitherto nonunderstood reasons, a molecular weight of 86 kDa in SDS-Polyacrymide gel while the calculated value is 71.4 kDa (F. Götz et al (1985), Complete nucleotide sequence of the lipase gene from *Staphylococcus hyicus* cloned in *Staphylococcus carnosus*. Nucl. Acids Res. 13, 3895–3906).

The results of the trypsin treatment indicated that the 82 kDa protein is apparently a nonprocessable precursor of the lipase OmpA fusion protein which accumulates in the cytoplasm. The processable form of the fusion protein, which is found in the cell protein fraction, can be reliably localized on the outer side of the plasma membrane since a greater part of this protein is dissolved already upon the protoplastization of the cell and the remaining portion is decomposed by trypsin. In either case the OmpA protein is not greater but secreted in soluble form into the medium with the aid of the lipase propeptide. Since *Staphylococcus carnosus* has very little protease activity in the culture supernatant, the hybrid protein remains stable in the medium over long periods.

While the propeptide, whose exact function has hitherto been unknown, in the normal case after transversing the membrane, can be split from the mature protein either autocatalytically or by the proteases present in the extracellular medium, the propeptide remains, in the example, bound to outer membrane protein. To achieve a splitting off also of the propeptide, a gene sequence can be produced by synthesis from oligonucleotides which codes for an amino acid sequence corresponding to a protease cleavage. The gene sequence can additionally be incorporated between the gene coding for the outer membrane protein and the progene sequence so that after liberation of the hybrid protein, it is treated with the corresponding protease. Thereafter it is possible to recover the mature outer membrane protein from the culture medium or supernatant.

We claim:

1. Process for producing outer membrane protein of Gram-negative bacteria recoverable from the culture supernatant, from Gram-positive host cells in which a gene structure is constructed which has an outer membrane protein coding gene from Gram-negative bacteria as well as a propeptide coding progene sequence for an export protein of a Gram-positive bacterium upstream of this outer membrane protein coding gene, and a pregene sequence coding for a signal peptide of an export protein of a Gram-positive bacterium upstream of the progene sequence, the gene structure is cloned in a vector and this is transformed in a Gram-positive bacteria as a host cell having substantially no protease activity in the culture supernatant, whereafter the Gram negative outer membrane protein is expressed as a fusion protein with the Gram positive signal peptide and the Gram positive propeptide, is transported through the membrane of the Gram-positive host cell and is liberated in the culture supernatant.

2. An isolated fusion protein comprising the Gram negative outer membrane protein with the Gram positive signal peptide and the Gram positive propeptide obtained by the process of claim 1.

3. A method of inoculating a host with an outer membrane protein from a Gram negative bacteria which comprises the step of administering to said host, the fusion protein comprising the Gram negative outer membrane protein expressed with Gram positive signal peptide and Gram positive propeptide obtained by the process of claim 1.

4. The process for producing an outer membrane protein defined in claim 1 which further comprises the step of:
    removing the signal peptide expressed with the outer membrane protein and the propeptide.

5. An isolated fusion protein comprising the Gram negative outer membrane protein with the Gram positive propeptide obtained by the process of claim 4.

6. A method of inoculating a host with an outer membrane protein from a Gram negative bacteria which comprises the step of administering to said host, the fusion protein comprising the Gram negative outer membrane protein expressed with Gram positive propeptide obtained by the process of claim 4.

7. A gene structure containing a gene coding for an outer membrane protein of Gram-negative bacteria and upstream of this gene, a progene sequence coding for a propeptide of an export protein of a Gram-positive bacteria and, upstream of the progene sequence, a pregene sequence coding for a signal peptide of an export protein of a Gram-positive bacteria.

8. A vector containing a gene structure according to claim 7.

9. Gram-positive host cells containing a gene structure according to claim 7 or a vector according to claim 3.

* * * * *